United States Patent
Lazar et al.

(10) Patent No.: US 9,014,216 B2
(45) Date of Patent: Apr. 21, 2015

(54) REAL-TIME TIME ENCODING AND DECODING MACHINES

(75) Inventors: Aurel A. Lazar, New York, NY (US); Erno K. Simonyi, Budapest (HU); Laszlo T. Toth, Budapest (HU); Ádám Tóth, legal representative, Budapest (HU); László Tiborné Tóth, legal representative, Budapest (HU)

(73) Assignee: The Trustees of Columbia University in the City of New York, New York, NY (US)

( * ) Notice: Subject to any disclaimer, the term of this patent is extended or adjusted under 35 U.S.C. 154(b) by 339 days.

(21) Appl. No.: 12/628,067

(22) Filed: Nov. 30, 2009
(Under 37 CFR 1.47)

(65) Prior Publication Data
US 2010/0303101 A1    Dec. 2, 2010

Related U.S. Application Data

(63) Continuation of application No. PCT/US2008/065542, filed on Jun. 2, 2008, which is a continuation-in-part of application No. 11/965,337, filed on Dec. 27, 2007, now Pat. No. 7,479,907.

(Continued)

(51) Int. Cl.
*H04J 3/00* (2006.01)
*A61B 5/00* (2006.01)
(Continued)

(52) U.S. Cl.
CPC .......... *A61B 5/0002* (2013.01); *A61B 5/04012* (2013.01); *H03M 1/125* (2013.01); *H03M 1/50* (2013.01); *H03M 1/82* (2013.01); *H03M 3/432* (2013.01); *H03M 3/502* (2013.01)

(58) Field of Classification Search
CPC . A61B 5/0002; A61B 5/04012; H03M 1/125; H03M 3/502; H03M 1/82; H03M 3/432; H03M 1/50
USPC ............ 370/521; 375/216, 316; 341/110, 155
See application file for complete search history.

(56) References Cited

U.S. PATENT DOCUMENTS

| | | |
|---|---|---|
| 5,079,551 A | 1/1992 | Kimura et al. |
| 5,200,750 A | 4/1993 | Fushiki et al. |

(Continued)

FOREIGN PATENT DOCUMENTS

| | | |
|---|---|---|
| WO | WO 2006/102178 | 9/2006 |
| WO | WO 2008/151137 | 12/2008 |

OTHER PUBLICATIONS

U.S. Appl. No. 12/645,292, filed Dec. 22, 2009.

(Continued)

*Primary Examiner* — Luat Phung
(74) *Attorney, Agent, or Firm* — Baker Botts L.L.P.

(57) ABSTRACT

Methods for decoding a signal encoded by a Time Encoding Machine (TEM) include defining a plurality of time-windows, each time-window corresponding to a portion of a TEM-encoded signal and made up of a plurality of trigger values, at least two of the time-windows overlapping, decoding each of the time-windows using a Time Decoding Machine (TDM) to generate a decoded time-window, and stitching the decoded time-windows together to generate a TEM-decoded signal.

15 Claims, 7 Drawing Sheets

Related U.S. Application Data

(60) Provisional application No. 60/987,477, filed on Nov. 13, 2007, provisional application No. 60/944,997, filed on Jun. 19, 2007, provisional application No. 60/976,675, filed on Oct. 1, 2007, provisional application No. 60/941,498, filed on Jun. 1, 2007.

(51) Int. Cl.
*H03M 1/12* (2006.01)
*H03M 1/82* (2006.01)
*H03M 3/00* (2006.01)
*A61B 5/04* (2006.01)
*H03M 1/50* (2006.01)

(56) References Cited

U.S. PATENT DOCUMENTS

| | | | |
|---|---|---|---|
| 5,392,042 | A | 2/1995 | Pellon |
| 5,392,044 | A | 2/1995 | Kotzin et al. |
| 5,393,237 | A | 2/1995 | Roy et al. |
| 5,396,244 | A | 3/1995 | Engel |
| 5,424,735 | A | 6/1995 | Arkas et al. |
| 5,511,003 | A | 4/1996 | Agarwal |
| 5,561,425 | A | 10/1996 | Therssen |
| 5,568,142 | A | 10/1996 | Velazquez et al. |
| 5,761,088 | A | 6/1998 | Hulyalkar et al. |
| 5,815,102 | A | 9/1998 | Melanson |
| 6,081,299 | A | 6/2000 | Kesselring et al. |
| 6,087,968 | A | 7/2000 | Roza |
| 6,121,910 | A | 9/2000 | Khoury et al. |
| 6,177,893 | B1 | 1/2001 | Velazquez et al. |
| 6,177,910 | B1 | 1/2001 | Sathoff et al. |
| 6,332,043 | B1 | 12/2001 | Ogata |
| 6,369,730 | B1 | 4/2002 | Blanken et al. |
| 6,441,764 | B1 | 8/2002 | Barron et al. |
| 6,476,749 | B1 | 11/2002 | Yeap et al. |
| 6,476,754 | B2 | 11/2002 | Lowenborg et al. |
| 6,511,424 | B1 | 1/2003 | Moore-Ede et al. |
| 6,515,603 | B1 | 2/2003 | McGrath |
| 6,646,581 | B1 | 11/2003 | Huang |
| 6,744,825 | B1 | 6/2004 | Rimstad et al. |
| 6,961,378 | B1 | 11/2005 | Greenfield et al. |
| 7,028,271 | B2 | 4/2006 | Matsugu et al. |
| 7,336,210 | B2 | 2/2008 | Lazar |
| 7,346,216 | B2 | 3/2008 | Adachi et al. |
| 7,479,907 | B2 | 1/2009 | Lazar et al. |
| 7,750,835 | B1 | 7/2010 | Albrecht et al. |
| 7,764,716 | B2 * | 7/2010 | McKnight et al. ............ 370/525 |
| 7,948,869 | B2 | 5/2011 | Petre et al. |
| 7,966,268 | B2 | 6/2011 | Anderson et al. |
| 8,023,046 | B2 | 9/2011 | Lazar et al. |
| 8,199,041 | B2 | 6/2012 | Nakajima |
| 8,223,052 | B1 | 7/2012 | Kong et al. |
| 8,314,725 | B2 | 11/2012 | Zepeda et al. |
| 8,595,157 | B2 | 11/2013 | Albrecht et al. |
| 2001/0044919 | A1* | 11/2001 | Edmonston et al. .......... 714/752 |
| 2004/0071354 | A1 | 4/2004 | Adachi et al. |
| 2004/0158472 | A1* | 8/2004 | Voessing ....................... 704/500 |
| 2005/0190865 | A1 | 9/2005 | Lazar et al. |
| 2005/0252361 | A1* | 11/2005 | Oshikiri ......................... 84/605 |
| 2006/0261986 | A1 | 11/2006 | Lazar |
| 2009/0141815 | A1 | 6/2009 | Peter et al. |
| 2009/0190544 | A1 | 7/2009 | Meylan et al. |
| 2010/0138218 | A1* | 6/2010 | Geiger .......................... 704/205 |
| 2010/0303101 | A1 | 12/2010 | Lazar et al. |
| 2012/0084040 | A1 | 4/2012 | Lazar et al. |
| 2012/0310871 | A1 | 12/2012 | Albrecht et al. |
| 2012/0317061 | A1 | 12/2012 | Lakshminarayan et al. |
| 2013/0311412 | A1 | 11/2013 | Lazar et al. |
| 2014/0267606 | A1 | 9/2014 | Lazar et al. |
| 2014/0279778 | A1 | 9/2014 | Lazar et al. |

OTHER PUBLICATIONS

U.S. Appl. No. 12/645,292, May 17, 2011 Notice of Allowance.
U.S. Appl. No. 12/645,292, Apr. 27, 2011 Response to Non-Final office Action.
U.S. Appl. No. 12/645,292, Jan. 7, 2011 Non-Final Office Action.
Lazar, .A.A., "Time encoding machines with multiplicative coupling, feedforward, and feedback", *Circuits and Systems II: Express Briefs, IEEE Transactions*, 53(8): 672-676, Aug. 2006.
Lazar, A.A., "Time encoding and perfect recovery of bandlimited signals", *Acoustics, Speech and Signal Processing, Proceedings (ICASSP 2003), 2003 IEEE International Conference*, 2003, vol. 6, pp. VI-709-712.
Lazar, A.A., "Time encoding using filter banks and integrate and fire neurons", Depar*tment of Electrical Engineering, Columbia University*, Sep. 2006.
Lazar et al..: "Perfect Recovery and Sensitivity Analysis of Time Encoded Bandlimited Signals" *IEEE Transactions on Circuits and Systems*, vol. 51, No. 10 pp. 2060-2073 (Oct. 2004).
Lazar et al. : "Real-Time Algorithm for Time Decoding Machines" *EUSIPCO '06* (Sep. 2006).
PCT Notification Concerning Transmittal of International Preliminary Report on Patentability and International Preliminary Report on Patentability; mailed on Dec. 10, 2009 by the International Bureau.
PCT Written Opinion of the International Searching Authority; mailed Nov. 25, 2008 by the International Searching Authority.
U.S. Appl. No. 14/216,255, filed Mar. 17, 2014.
U.S. Appl. No. 14/218,736, filed Mar. 18, 2014.
U.S. Appl. No. 13/214,041, Jun. 25, 2014 Final Office Action.
U.S. Appl. No. 13/214,041, Jun. 9, 2014 Response to Non-Final Office Action.
U.S. Appl. No. 13/948,615, filed Jul. 23, 2013.
U.S. Appl. No. 13/948,615, Dec. 18, 2013 Non-Final Office Action.
U.S. Appl. No. 13/214,041, Dec. 24, 2013 Non-Final Office Action.
Akay, "Time Frequency and Wavelets in Biomedical signal Processing", *Wiley-IEEE Press*, Table of Contents (1997) Retrieved at http://www.wiley.com/WileyCDA/WileyTitle/productCd-0780311477,miniSiteCd-IEEE2 on Aug. 6, 2008.
Aksenov, et al., "Biomedical Data Acquisition Systems Based on Sigma-Delta Analogue-To Digital converters", *2001 Proceedings of the 23rd Annual EMBS International Conference*, Istanbul, Turkey, 4:3336-3337 (Oct. 25-28, 2001).
Antoine, et al., "Two-Dimensional Wavelets and Their Relatives", *Cambridge University Press*, Table of Contents (2004).
Averbeck, et al., "Neural Correlations, Population Coding and Computation", *Nature*, 7:358-366 (2006).
Balan, et al., "Multiframes and Multi Riesz Bases: I. The General theory and Weyl-Heisenberg Case", *Technical Report, Institute for mathematics and its Applications*, (18 pages) (1997).
Balan, "Multiplexing of Signals using Superframes", *Wavelets Applications in Signal and Image Processing VIII*, 4119:118-130 (2000).
Barr, et al., "Energy Aware Lossless Data Compression", *Proceedings of the 1st International Conference on Mobile Systems, Applications and Services*, San Francisco, CA, pp. 231-244 (2003).
Bjorck, et al., "Solution of Vandermonde Systems of Equations", *Mathematics of Computation*, 24(112):893-903 (1970).
Butts, et al., "Temporal Precision in the Neural code and the Timescales of Natural Vision", *Nature*, 449(7158):92-95 (2007).
Christensen, "Frames, Riesz Bases, and Discrete Gabor/Wavelet Expansions", *American Mathematical Society*, 38(3):273-291 (2001).
Christensen, "An Introduction to Frames and Riesz Bases", *Springer*, Table of Contents (2003) http://www.springer.com/birkhauser/mathematics/books/978-0-8176-4295-2?detailsPage=toc Retrieved on Aug. 6, 2008.
Dayan et al., "Theoretical Neuroscience", *The MIT Press*, Table of Contents (2001) http://mitpress.mit.edu/catalog/item/default.asp?ttyoe=2&tid=8590&mode=toc Retrieved on line Aug. 6, 2008.
Delbruck, "Frame-Free Dynamic Digital Vision", *Proceedings of international Symposium on Secure-Life Electronics, Advanced Electronics for Quality Life and Society*, University of Tokyo, pp. 21-26 (Mar. 6-7, 2008).
Deneve, et al., "Reading Population Codes: A Neural Implementation of Ideal Observers", *Nature Neuroscience*, 2(8):740-745 (1999).

(56) References Cited

OTHER PUBLICATIONS

Dods, et al., "Asynchronous Sampling for Optical Performance Monitoring", *Optical fiber Communication Conference*, Anaheim, California (3 pages) (2007).
Eldar, et al., "Sampling with Arbitrary Sampling and Reconstruction Spaces and Oblique dual Frame Vectors", *The Journal of Fourier Analysis and Applications*, 9(1):77-96 (2003).
Eldar, et al., "General Framework for Consistent Sampling in Hilbert Spaces", *International journal of Wavelets, Multiresolution and information Processing*, 3(3):347-359 (2005).
Fain, "Sensory Transduction", *Sinauer Associates, Inc.*, Table of contents (2003) Retrieved http://www.sinauer.com/detail.php?id=1716 on Aug. 6, 2008.
Feichter, et al., "Theory and Practice of Irregular Sampling", *Wavelets: Mathematics and Applications, CRC Press, Studies in Advanced Mathematics*, pp. 305-363 (1994).
Feichter, et al., "Efficient Numerical Methods in Non-Uniform Sampling Theory", *Numer. Math.*, 69:423-440 (1995).
Feichter, et al., "Improved Locality for Irregular Sampling Algorithms", *2000 International Conference on Acoustic, Speech, and Signal Processing*, Istanbul, Turkey, Table of Contents (Jun. 5-9, 2000).
Field, et al., "Information Processing in the Primate Retina: Circuitry and Coding", *Annual Reviews Neuroscience*, 30(1):1-30 (2007).
Häfliger, et al., "A Rank Encoder: Adaptive Analog to Digital conversion Exploiting Time Domain Spike Signal Processing", *Analog Integrated Circuits and Signal Processing Archive*, 40(1):39-51 (2004).
Han, et al., "Memoirs of the American Mathematical Society: Frames, Baese and Group Presentations", *American Mathematical Society*, 147(697): Table of Contents (2000).
Harris, et al., "Real Time Signal Reconstruction from Spikes on a Digital Signal Processor", *IEEE International Symposium on Circuits and Systems (ISCAS 2008)*, pp. 1060-1063 (2008).
Haykin, et al., "Nonlinear Adaptive Prediction of Nonstationary Signals", *IEEE Transactions on Signal Processing*, 43(2):526-535 (1995).
Hudspeth, et al., "Auditory Neuroscience: Development, Transduction, and Integration", *PNAS*, 97(22):11690-11691 (2000).
Jaffard, "A Density Criterion for Frames of Complex Exponentials", *Michigan Math J.*, 38:339-348 (1991).
Jones, et al., "An Evaluation of the Two-Dimensional Gabor Filter Model of Simple Receptive Fields on Cat Striate Cortex", *Journal of Neurophysiology*, 58(6):1233-1258 (1987).
Jovanov, et al., "A Wireless Body Area network of Intelligent motion sensors for computer Assisted Physical Rehabilitation", *Journal of NeuroEngineering and Rehabiliation*, 2:6 (10 pages) (2005).
Kaldy, et al., "Time Encoded Communications for Human Area Network Biomonitoring", *BNET Technical Report #2-7, Department of Electrical Engineering, Columbia University*, (8 pages) (2007).
Keat, et al., "Predicting Every Spike: A Model for the Responses of Visual Neurons", *Neuron*, 30:803-817 (2001).
Kim, et al., "A Comparison of Optimal MIMO Linear and Nonlinear Models for Brain-Machine Interfaces", *Journal of Neural Engineering*, 3:145-161 (2006).
Kinget, et al., "on the Robustness of an Analog VLSI Implementation of a Time Encoding Machine", *IEEE International Symposium on Circuits and Systems*, pp. 4221-4224 (2005).
Kong, et al., "A Time-Encoding Machine Based High-Speed Analog-to-Digital Converter", *IEEE Journal on Emerging and Selected Topics in Circuits and Systems*, 2(3):552-563 (2012).
Kovacevic, et al., "Filter Bank Frame Expansions with Erasures", *IEEE Transactions on Information Theory*, 48(6):1439-1450 (2002).
Krishnapura, et al., "A Baseband Pulse Shaping Filter for Gaussian Minimum Shift Keying", *ISCAS '98, IEEE International Symposium on circuits and Systems*, vol. 1:249-252 (1998).
Lazar, et al., "Encoding, Processing and Decoding of Sensory Stimuli with a Spiking Neural Population", *Research in encoding and Decoding of Neural Ensembles*, Santiori, Greece, (1 page) (Jun. 26-29, 2008).

Lazar, "A Simple Spiking Retina Model for Exact Video Stimulus Representation", *The Computational Neuroscience Meeting, CNS 2008*, Portland, Oregon (1 page) (Jul. 19-24, 2008).
Lazar, et al., "Time Encoding and Time Domain Computing of Video Streams", *Department of Electrical engineering Columbia University*, (20 pages) (Mar. 14, 2008).
Lazar, et al., "A MIMO Time Encoding Machine", submitted for publication Jan. 2008, (28 pages).
Lazar, et al., "Encoding of Multivariate Stimuli with MIMO Neural Circuits", *Proceedings of the IEEE International Symposium on Information Theory*, Saint Petersburg, Russia, (5 pages) (Jul. 31-Aug. 5, 2011).
Lazar, et al., "Video Time Encoding Machines", submitted for publication Oct. 2008, (27 pages).
Lazar, et al., "Channel Identification Machines", *Computational Intelligence and Neuroscience*, 2012:209590 (20 pages) (2012).
Lazar, "Multichannel Time Encoding with Integrate-and-Fire Neurons", *Neurocomputing*, 65-66:401-407 (2005).
Lazar, "Recovery of Stimuli Encoded with Hodgkin-Huxley Neurons", *Computational and Systems Neuroscience Meeting, COSYNE 2007*, Salt Lake City, UT, Feb. 22-25, 2007, *Cosyne Poster III-94*, p. 296.
Lazar, "Time Encoding with an Integrate-and-Fire Neuron with a Refractory Period", *Neurocomputing*, 58-60:53-58 (2004).
Lazar, et al., "Video Time Encoding Machines", *IEEE Transactions on Neural Networks*, 22(3):461-473 (2011).
Lazar, "Population Encoding with Hodgkin-Huxley Neurons", *IEEE Transactions on Information Theory*, 56(2):821-837 (2010).
Lazar, "Information Representation with an Ensemble of Hodgkin-Huxley Neurons", *Neurocomputing*, 70:1764-1771 (2007).
Lazar, et al., "Encoding Natural Scenes with Neural circuits with Random Thresholds", *Vision Research, Special Issue on Mathematical Models of Visual Coding*, 50(22):2200-2212 (2010).
Lazar, "A Simple Model of Spike Processing", *Neurocomputing*, 69:1081-1085 (2006).
Lazar, et al., "Faithful Representation of Stimuli with a Population of Integrate-and-Fire Neurons", *Neural Computers*, 20(11):2715-2744 (2008).
Lazar, et al., "An Overcomplete Stitching Algorithm for Time Decoding Machines", *IEEE Transactions on Circuits and Systems-I*, (11 pages) (2008).
Lazar, et al., "Fast Recovery Algorithms for Time Encoded Bandlimited Signals", *Proceeding of the International Conference on acoustics, Speech and Signal Processing (ICASSP '05)*, Philadelphia, PA, Mar. 19-23, 2005, 4:237-240 (2005).
Lee, "Image Representation using 2D Gabor Wavelets", *IEEE Transactions on Pattern Analysis and Machine Intelligence*, 18(10):959-971 (1996).
Lichtsteiner, et al., "A 128X128 120db 15 µs Latency Asynchromous Temporal Contrast Vision Sensor", *IEEE Journal of solid-State Circuits*, 43(2):566-576 (2008).
Masland, "The Fundamental Plan of the Retina", *Nature Neuroscience*, 4(9):877-886 (2001).
MIT-BIH Arrhythmia Database, http://www.physionet.org/physiobank/database/mitd Retrieved on Aug. 5, 2008 (3 pages).
Olshausen, "Sparse Codes and Spikes", In R.P.N. Rao, B.A. Olshausen and M.S. Lewicki, editors, Probabilistic Models of Perception and Brian Function, *MIT Press*, (15 pages) (2002).
Olshausen, et al., "Sparse Coding with an Overcomplete Basis Set: A Strategy Employed by V1?", *Vision research*, 37(23):3311-3325 (1997).
Ouzounov, et al., "Analysis and Design of High-Performance Asynchronous Sigma-Delta Modulators with a Binary Quantizer", *IEEE Journal of Solid-State Circuits*, 41(3):588-596 (2006).
Papoulis, "Generalized Sampling Expansion", *IEEE Transactions on Circuits and Systems*, CAS-24(11):652-654 (1977).
"Parks-McClellan FIR filter Design" (Java 1.1 version) http://www.dsptutor.freeuk.com/remez/RemezFIRFilterDesign.htlm. Retrieved on Aug. 5, 2008.
Patterson, et al., "Complex Sounds and Auditory Images", *Advances in the biosciences*, 83:429-446 (1992).

(56) References Cited

OTHER PUBLICATIONS

Pillow, et al., "Prediction and Decoding of Retinal Ganglion Cell Responses with a Probabilistic Spiking Model", *The Journal of Neuroscience*, 25(47):11003-11013 (2005).

Roza, "Analog-to-Digital conversion Via Duty-Cycle Modulation", *IEEE Transactions on Circuits and Systems II: Analog and Digital Signal Processing*, 44(11):907-917 (1997).

Sanger, "Neural Population Codes", *Current Opinion in Neurobiology*, 13:238-249 (2003).

Seidner, et al., "Vector Sampling Expansion", *IEEE Transactions on Signal Processing*, 48(5):1401-1416 (2000).

Shang, et al., "Vector Sampling Expansions in shift Invariant Subspaces", *J. Math. Anal. Appl.*, 325:898-919 (2007).

Sheung, "A Continuous-Time Asynchronous Sigma Delta Analog to Digital Converter for Broadband Wireless Receiver with Adaptive Digital Calibration Technique", *PhD Thesis, Department of Electrical and Computer Engineering*, Ohio State University, (137 pages) (2009).

Shinagawa, et al., "A Near-Field-Sensing Transceiver for Intrabody Communication Based on the Electrooptic Effect", *IEEE Transactions on Instrumentation and Measurement*, 53(6):1533-1538 (2004).

Slaney, "Auditory Toolbox", *Technical Report #1998-010, Interval Research Corporation*, (52 pages) (1998).

Strohmer, "Numerical Analysis of the Non-Uniform Sampling Problem", *Journal of Computational and Applied Mathematics*, 122:297-316 (2000).

Strohmer, "Irregular Sampling, Frames and Pseudoinverse", *Master Thesis, dept. Math. Univ.*, Vienna, Austria, (Abstract) (1991).

Teolis, "Computational signal Processing with Wavelets", *Applied and Numerical Harmonic Analysis*, Chapter 4-6, pp. 59-167 (1998).

Topi, et al., "Spline Recurrent Neural Networks for Quad-Tree Video Coding", *WIRN VIETRI, Springer-Verlag, LNCS 2486*, pp. 90-98 (2002).

Venkataramani, et al., "Sampling Theorems for Uniform and Periodic Nonuniform MIMO Sampling of Multiband Signals", *IEEE Transactions on Signal Processing*, 51(12):3152-3163 (2003).

Wei, et al., "Signal Reconstruction from Spiking Neuron Models", *Proceedings of the ISCAS '04*, vol. V:353-356 (May 23-26, 2004).

Wolfram, "Mathematic 5.2", The Mathematica Book Online, http://documents.wolfram.com/mathematica Retrieved on Aug. 5, 2008.

Yang, et al., "A Bio-Inspired Ultra-Energy-Efficient Analog-to-Digital converter for Biomedical Applications", *IEEE Transactions on Circuits and Systems-I: Regular Papers*, 53(11):2349-2356 (2006).

Zimmerman, "Personal Area Networks (PAN): Near-field Intra-Body Communication", *MS Thesis, MIT*, (81 pages) (1995).

Zimmerman, "Personal Area Networks: Near-field Intrabody Communication", *IBM systems Journal*, 35(3&4):609-617 (1996).

\* cited by examiner

REAL-TIME TIME ENCODING AND DECODING MACHINES

CROSS REFERENCE TO RELATED APPLICATIONS

This application claims priority from, and is a Continuation of: International Application No. PCT/US08/65542 filed on Jun. 2, 2008, which itself claims priority from: U.S. patent application Ser. No. 11/965,337 filed on Dec. 27, 2007; U.S. Provisional Patent Application No. 60/941,498 filed on Jun. 1, 2007; U.S. Provisional Patent Application No. 60/944,997 filed on Jun. 19, 2007; U.S. Provisional Patent Application No. 60/976,675 filed on Oct. 1, 2007; and U.S. Provisional Patent Application No. 60/987,477 filed on Nov. 13, 2007, the entire disclosures of which are incorporated by reference herein.

STATEMENT REGARDING FEDERALLY SPONSORED RESEARCH

This invention was made with government support under grant No. CCF-06-35252, awarded by the National Science Foundation. The government has certain rights in the invention.

BACKGROUND

1. Field

The present application relates to methods and systems for Time Encoding Machines and Time Decoding Machines.

2. Background Art

Most signals in the natural world are analog, i.e., cover a continuous range of amplitude values. However, most computer systems for processing these signals are binary digital systems. Generally, synchronous analog-to-digital (A/D) converters are used to capture analog signals and present a digital approximation of the input signal to a computer processor. That is, at precise moments in time synchronized to a system clock, the amplitude of the signal of interest is captured as a digital value. When sampling the amplitude of an analog signal, each bit in the digital representation of the signal represents an increment of voltage, which defines the resolution of the A/D converter. Analog-to-digital conversion is used in numerous applications, such as communications where a signal to be communicated can be converted from an analog signal, such as voice or video, to a digital signal prior to transport along a transmission line or other transmission means.

Applying traditional sampling theory, a band limited signal can be represented with a quantifiable error by sampling the analog signal at a sampling rate at or above what is commonly referred to as the Nyquist sampling rate. It is a continuing trend in electronic circuit design to reduce the available operating voltage provided to integrated circuit devices. In this regard, power supply voltages for circuits are constantly decreasing. While digital signals can be processed at the lower supply voltages, traditional synchronous sampling of the amplitude of a signal becomes more difficult as the available power supply voltage is reduced and each bit in the A/D or D/A converter reflects a substantially lower voltage increment.

SUMMARY

Systems and methods for using Time Encoding and Decoding Machines are disclosed herein.

In some embodiments, systems for decoding a signal encoded by a Time Encoding Machine (TEM) include a Time Decoding Machine (TDM) for decoding a portion of a TEM-encoded signal, the TDM having a TDM-input and a TDM-output, the TDM-input for receiving a portion of a TEM-encoded signal over a first time-window, the TDM-output for transmitting a decoded approximated signal over the first time-window, and a stitching circuit, having a stitching-input connected to the TDM-output, the stitching circuit combining the decoded approximated signal over the first time-window with at least one other decoded approximated signal over a second time-window, where the first time-window and said second time-window overlap. In some embodiments, the TDM calculates a value of the TEM-encoded signal, u, over the first time-window, $[t_i, t_{i+N}]$, wherein the value of u at a given time, t, is approximated by solving for a periodic band-limited signal $$u_i(t) = \sum_{n=0}^{N} j\left(\Omega - n\frac{2\Omega}{N}\right) d_{i,n} e^{j(-\Omega + n\frac{2\Omega}{N})t},$$

where the bandwidths of each period of $u_i(t)$ are $\Omega$ and $2N\pi/\Omega$ (for $N \geq 1$), respectively, coefficients $[d_i]_n = d_{i,n}$, and $d_i$ is solved by letting $z_n^m = e^{jm2\Omega t_{i+n}/N}$ where n, m=0,1, ... N, and solving for a vector b such that
    for n=0, ..., N−2 do:
    for m=N, ..., n+1 do:

$$b_m = (b_m - b_{m-1})/(z_m - z_{m-n-1})$$

for n=N−2, ..., 0 do:
    for m=n, ..., N−2 do:

$$b_m = b_m - b_{m+1} z_n$$

and letting $d_i = b$. In further embodiments, $$d_i = b\left(x_i - \frac{1}{\alpha_i} y_i y_i^H x_i\right),$$

for $\alpha_i = y_i^H y_i$ and $x_i$ and $y_i$ denote solutions of Vandermonde systems $V_i x_i = D_i(P - ab^H) r_i$ and $V_i y_i = D_i a_i$ respectively, where $[V_i]_{nm} = e^{jm2\Omega t_{i+n}/N}$ is a Vandermonde matrix, $D_i = \text{diag}(e^{j\Omega t_{i+n}})$ is a diagonal matrix, P is an upper triangular matrix with values $[P]_{nm} = 1$ and $[P]_{nm} = 0$ for $n < m+1$ and $n \geq m+1$, $[r_i]_n = (-1)^{i+n+1} T_{i+n}$, $a^H = [\ldots, 0, 1, 0, 1]$, and $b^H = [0, \ldots, 0, 0, 1]$.

In some embodiments, the coefficients $[d_i]_n = d_{i,n}$ can be recovered by solving equation $V_i^H V_i d_i = V_i^H D_i P q_i$, where $V_i^H$ is a conjugate transposition of $V_i$, $[V_i]_{nm} = e^{jm2\Omega t_{i+n}/N}$ is a Vandermonde matrix, $D_i = \text{diag}(e^{j\Omega t_{i+n}})$ is a diagonal matrix, P is an upper triangular matrix with values $[P]_{nm} = 1$ and $[P]_{nm} = 0$ for $n < m+1$ and $n \geq m+1$, respectively and $[q_i]_n = q_i + n$, for all n, m=0, ..., N.

In some embodiments, the first and second time-windows, $\omega_n$, can be defined by a function $$\omega_n(t) = \begin{cases} 0 & \text{if } t \notin (\tau_n, \sigma_{n+1}], \\ \theta_n(t) & \text{if } t \in (\tau_n, \sigma_n], \\ 1 & \text{if } t \in (\sigma_n, \tau_{n+1}], \\ 1 - \theta_{n+1}(t) & \text{if } t \in (\tau_{n+1}, \sigma_{n+1}] \end{cases},$$

where K represents a value of desired overlapping trigger times, J=N−2M−K, $\tau_n = t_{nJ+M}$, $\sigma = t_{nJ+M+K}$, N represents a number of trigger times and $$\theta_n(t) = \sin^2\left(\frac{\pi}{2} \cdot \frac{t - \tau_n}{\sigma_n - \tau_n}\right).$$

The stitching circuit can combine the first and second time-windows by solving equation $$\hat{u}(t) = \sum_{n \in \mathbb{Z}} \omega_n(t) u_{nJ}(t).$$

Some embodiments include a post-filtering circuit connected to an output of the stitching circuit for receiving a combined TEM-decoded signal, the post-filtering circuit removing an approximate error, $e[k]=u(kS)-\hat{u}(kS)$, from the combined TEM-decoded signal of the stitching circuit by solving for an equation $$e^{ap}[k] = \sum_{n \in \mathcal{J}} \omega_n(kS) e_{nJ}^{ap}(kS),$$

where S represents a sampling rate of the TEM-encoded signal.

Some methods for decoding a signal encoded by a Time Encoding Machine (TEM) include defining a plurality of time-windows, each time-window corresponding to a portion of a TEM-encoded signal and made up of a plurality of trigger values, at least two of the time-windows overlapping, decoding each of the time-windows using a Time Decoding Machine (TDM) to generate a decoded time-window, and stitching the decoded time-windows together to generate a TEM-decoded signal. In some embodiments, each of the time-windows overlaps with at least one other time-window. In further embodiments, the TDM calculates a value of the TEM-encoded signal, u, over one of the time-windows, $[t_i, t_{i+N}]$, where the value of u at a given time, t, is approximated by solving for periodic bandlimited signal $$u_i(t) = \sum_{n=0}^{N} j\left(\Omega - n\frac{2\Omega}{N}\right) d_{i,n} e^{j(-\Omega + n\frac{2\Omega}{N})t},$$

where the bandwidths of each period of $u_i(t)$ are $\Omega$ and $2N\pi/\Omega$ (for $N \geq 1$), respectively, the coefficients $[d_i]_n = d_{i,n}$, and $d_i$ can be solved by letting $z_n^m = e^{jm2\Omega t_{i+n}/N}$ where n, m=0,1,... N, and solving for a vector b such that for n=0, ..., N−2 do:
for m=N, ..., n+1 do:

$$b_m = (b_m - b_{m-1})/(z_m - Z_{m-n-1})$$

for n=N−2, ..., 0 do:
for m=n, ..., N−2 do:

$$b_m = b_m - b_{m+1} z_n$$

and $d_i = b$.
In some embodiments $$d_i = b\left(x_i - \frac{1}{\alpha_i} y_i Y_i^H x_i\right),$$

for $\alpha_i = y_i^H y_i$ and $x_i$ and $y_i$ denote solutions of Vandermonde systems $V_i x_i = D_i(P-ab^H) r_i$ and $V_i y_i = D_i a$, respectively, where $[V_i]_{nm} = e^{jm2\Omega t_{i+n}/N}$ is a Vandermonde matrix, $D_i = \text{diag}(e^{j\Omega t_{i+}})$ is a diagonal matrix, P is an upper triangular matrix with values $[P]_{nm}=1$ and $[P]_{nm}=0$ for $n < m+1$ and $n \geq m+1$, $[r_i]_n = (-1)^{i+n+1} T_{i+n}, a^H = [\ldots, 0, 1, 0, 1]$, and $b^H = [0, \ldots, 0, 0, 1]$.

In further embodiments the coefficients $[d_i]_n = d_{i,n}$ can be recovered by solving equation $V_i^H V_i d_i = V_i^H D_i P q_i$, where $V_i^H$ is a conjugate transposition of $V_i$, $[V_i]_{nm} = e^{jm2\Omega t_{i+n}/N}$ is a Vandermonde matrix, $D_i = \text{diag}(e^{j\Omega t_{i+n}})$ is a diagonal matrix, P is an upper triangular matrix with values $[P]_{nm}=1$ and $[P]_{nm}=0$ for $n<m+1$ and $n \geq m+1$, respectively and $[q_i]_n = q_i + n$, for all n, m=0, ..., N.

In some embodiments, the time-windows, $\omega_n$, can be defined by a function $$\omega_n(t) = \begin{cases} 0 & \text{if } t \notin (\tau_n, \sigma_{n+1}], \\ \theta_n(t) & \text{if } t \in (\tau_n, \sigma_n], \\ 1 & \text{if } t \in (\sigma_n, \tau_{n+1}], \\ 1 - \theta_{n+1}(t) & \text{if } t \in (\tau_{n+1}, \sigma_{n+1}] \end{cases},$$

where K represents a value of desired overlapping trigger times, $J=N-2M-K, \tau_n = t_{nJ+M}, \sigma = t_{nJ+M+K}$, N represents a number of trigger times and $$\theta_n(t) = \sin^2\left(\frac{\pi}{2} \cdot \frac{t - \tau_n}{\sigma_n - \tau_n}\right).$$

In some embodiments, stitching can be accomplished by solving the equation $$\hat{u}(t) = \sum_{n \in \mathbb{Z}} \omega_n(t) u_{nJ}(t).$$

Some embodiments further include post-filtering the TEM-decoded signal by removing an approximate error, $e[k]=u(kS)-\hat{u}(kS)$, from the TEM-decoded signal by solving for an equation $$e^{ap}[k] = \sum \omega_n(kS) e_{nJ}^{ap}(kS),$$

where S represents a sampling rate of the TEM-encoded signal.

Systems for transmitting data using a human body include a first data source holding data to be transmitted connected to a Time Encoding Machine (TEM), the TEM comprising an input and an output, the input for receiving the data to be transmitted from the data source and the output connected to a first body interface mechanism, the first body interface mechanism comprising an input for receiving TEM-encoded data to be transmitted, the body interface mechanism in connection with a first part of a human body for transmitting the TEM-encoded data, a second body interface mechanism in connection with a second part of the human body for receiving the TEM-encoded data, the second body interface mechanism comprising an output in connection with a data destination, and the data destination in communication with a Time Decoding Machine for decoding the TEM-encoded data.

In accordance with such systems, the first data source can be a pacemaker, glucose monitor, pulseoximeter, electrocardiography device, electroencephalography device, MP3 device, or mobile phone device.

In some embodiments, the TEM can be an integrate and fire neuron circuit or an asynchronous sigma/delta modulator. In further embodiments, the TEM can have multiplicative coupling and/or feedback.

In some embodiments, the part of a human body is skin and the first and second body interface mechanisms further include an insulator in physical contact with the skin. In further embodiments, the first body interface further comprises an AM modulator for modulating the TEM-encoded data prior to transmission through the insulator and the second body interface further comprises an AM demodulator for demodulating the TEM-encoded data prior to transmitting the TEM-encoded data to the data destination.

Some systems for transmitting data across a HAN further include a data collection device included in the data destination, the data collection device comprising a TDM for decoding the TEM-encoded signal. In further embodiments, the data collection device further includes a data storage area for storing an output of the TDM.

The accompanying drawings, which are incorporated and constitute part of this disclosure, illustrate preferred embodiments of the disclosed subject matter and serve to explain its principles.

Figure 1:
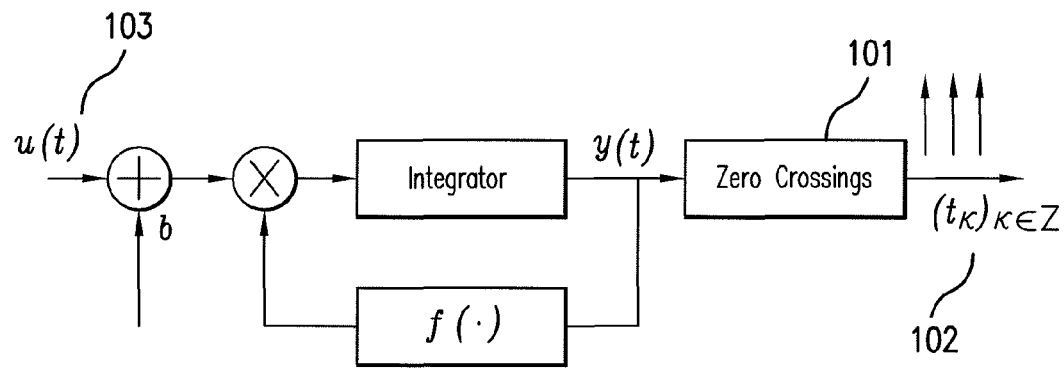
FIG. 1 depicts a Time Encoding Machine with Multiplicative Coupling in accordance with some embodiments of the disclosed subject matter.

Throughout the drawings, the same reference numerals and characters, unless otherwise stated, are used to denote like features, elements, components or portions of the illustrated embodiments. Moreover, while the present disclosed subject matter will now be described in detail with reference to the Figs., it is done so in connection with the illustrative embodiments.

DETAILED DESCRIPTION

Improved systems, methods, and applications of Time Encoding and Decoding machines are disclose herein. The methods and systems disclosed improve recovery of Time Encoding Machine-encoded signals and enhance the data transmission capabilities of a Human Area Network.

Time encoding is a real-time asynchronous mechanism of mapping the amplitude of a bandlimited signal $u(t)$, $t\in\mathbb{R}$, into a strictly increasing time sequence $(t_k)$, $k\in\mathbb{Z}$, where $\mathbb{R}$ and $\mathbb{Z}$ denote the sets of real numbers and integers, respectively. A Time Encoding Machine (TEM) is the realization of an asynchronous time encoding mechanism. A Time Decoding Machine (TDM) is the realization of an algorithm for signal recovery with arbitrary accuracy. With increasing device speeds TEMs are able to better leverage a temporal model of encoding a signal. The interest in temporal encoding in neuroscience is closely linked with the natural representation of sensory stimuli (signals) as a sequence of action potentials (spikes). Spikes can be discrete time events that carry information about stimuli. While in some embodiments the time of every spike, or trigger, can be recorded, in other embodiments, the number of spikes, or triggers, within each of a given time unit can be recorded.

Figure 3:
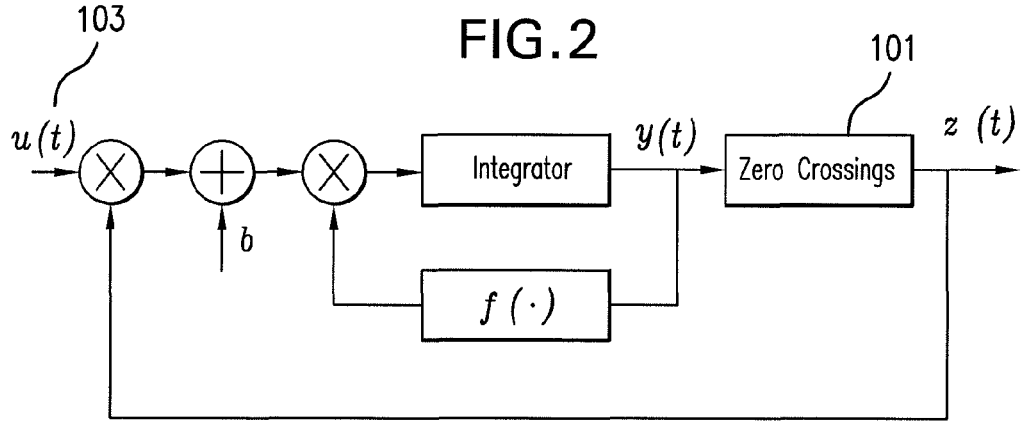
FIG. 3 depicts a Time Encoding Machine with multiplicative coupling and feedback in accordance with some embodiments of the disclosed subject matter.
Figure 4:
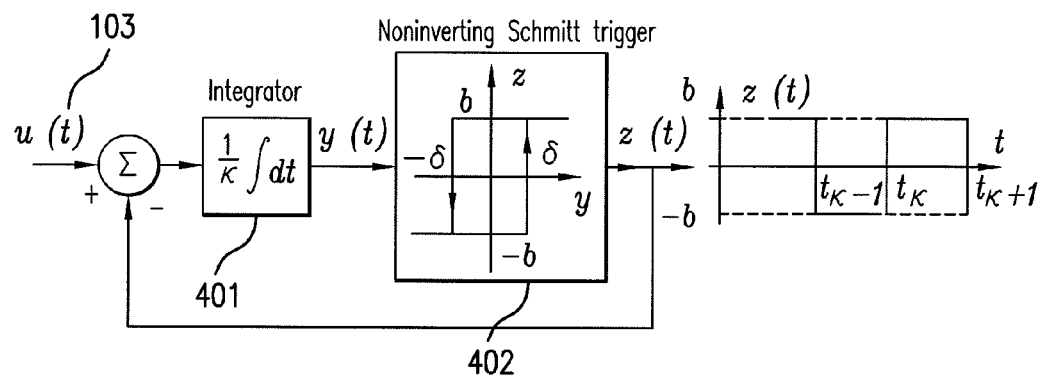
FIG. 4 depicts a Time Encoding Machine realized as an asynchronous sigma/delta modulator with $2\kappa\delta=\delta_{k+1}\delta_k, k\in\mathbb{Z}$, in accordance with some embodiments of the disclosed subject matter.

A general class of TEMs that exhibit multiplicative coupling and feedforward and feedback include those described in A. A. Lazar, "Time Encoding Machines with Multiplicative Coupling, Feedforward and Feedback", *IEEE Transactions on Circuits and Systems-II: Express Briefs*, Vol. 53, No. 8, pp. 672-676, August 2006 ("Lazar IEEE"), which is incorporated by reference. As depicted in FIG. 1, the basic underlying circuit consists of an oscillator whose output feeds a zero crossings detector 101. The detector generates the time sequence of the zeros 102 of the oscillator waveform. The oscillator is in turn modulated by an input bandlimited signal 103. As described in Lazar IEEE, TEMs with multiplicative coupling are I/O equivalent with simple nonlinear circuits. The TEM shown in FIG. 1 is I/O equivalent with an integrate-and-fire neuron with variable threshold depicted in FIG. 2. The variable threshold sequence is given by the difference between the consecutive zeros of the waveform generated by the oscillator for unit input. The same result holds for a TEM with feedforward while a TEM with feedback, as depicted in FIG. 3 is I/O equivalent with an asynchronous sigma/delta modulator with variable thresholds, as depicted in FIG. 4.

For the TEMs considered, the bandlimited signal at the input can be perfectly recovered from the zero crossings of the modulated signal and the threshold sequence. Perfect reconstruction can be achieved provided that a Nyquist-type rate condition is satisfied. Although methods used in frame theory and irregular sampling can be used to establish these conditions, as described by A. A. Lazar and L. T. Tóth, "Perfect Recovery and Sensitivity Analysis of Time Encoded Bandlimited Signals", *IEEE Transactions on Circuits and Systems-I: Regular Papers*, Vol. 51, No 10, pp. 2060-2073, October 2004 and A. A. Lazar, "Time Encoding with an Integrate-and-Fire Neuron with a Refractory Period", *Neurocomputing*, Vol. 58-60, pp. 53-58, 2004, which are incorporated by reference, the algorithms can be easy to find and only require solving a consistent but (typically) ill-conditioned infinite-dimensional system of linear equations.

Figure 2:
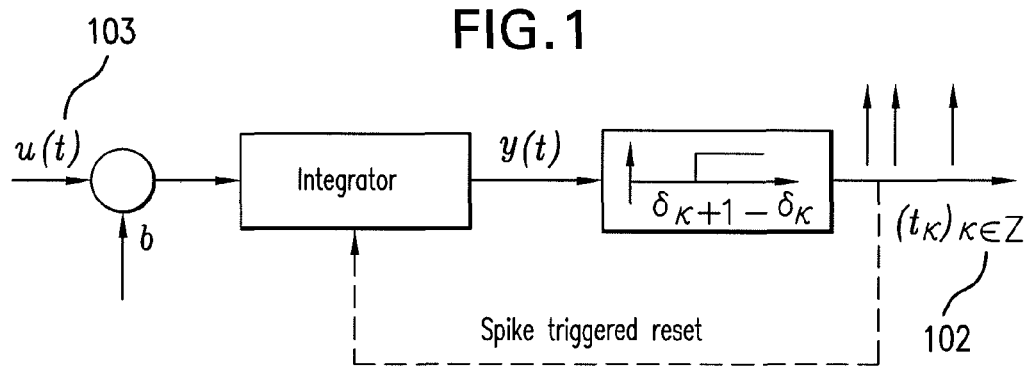
FIG. 2 depicts an Integrate-and-Fire Neuron with variable threshold in accordance with some embodiments of the disclosed subject matter.

As stated above, FIG. 1 depicts a TEM with multiplicative coupling that is I/O equivalent with an integrate-and-fire (IAF) neuron with the variable threshold sequence $\delta_{k+1}\delta_k$, as depicted in FIG. 2. The sequence $(\delta_k), k\in\mathbb{Z}$, represents the set of zeros of the oscillator waveform in FIG. 1. The analytical characterization of the IAF neuron is given by:

$$\int_{t_k}^{t_{k+1}} u(s)ds = \delta_{k+1} - \delta_k - b(t_{k+1}-t_k) \quad (1)$$

where $u=u(t), t\in\mathbb{R}$, is the output time sequence. The elements of the time sequence can also be referred to as trigger times. The input signal is assumed to be bounded in amplitude $|u(t)|\leq c<b$, has finite energy on $\mathbb{R}$ and is bandlimited to $|-\Omega, \Omega|$.

FIG. 3 depicts a TEM with multiplicative coupling and feedback. This circuit is I/O equivalent with the asynchronous sigma/delta modulator (ASDM), an example of which is depicted in FIG. 4, that is analytically described by:

$$\int_{t_k}^{t_{k+1}} u(s)ds = (-1)^k[\delta_{k+1} - \delta^k - b(t_{k+1} - t_k)] \quad (2)$$

with $y(t_0) = -(\delta_1 - \delta_0)$. Equations 1 and 2 are instantiations of the t-transform and map the amplitude information contained in the bandlimited signal $u = u(t)$, $t \in \mathbb{Z}$, into the increasing time sequence $(t_k)$, $k \in \mathbb{Z}$.

In one embodiment, the class the class of TEMs under consideration can be I/O equivalent with a nonlinear circuit with input $u(t)$, $t \in \mathbb{R}$, and output $(t_k)$, $k \in \mathbb{Z}$, that satisfies the t-transform $\int_{t_k}^{t_{k+1}} u(s)ds = q_k$, where $q_k$ is a function of $t_k$ and $t_{k+1}$ with $t_{k+1} > t_k$, $k \in \mathbb{Z}$. While the $q_k$ functions of Equations 1 and 2 are linear, nonlinear $q_k$, $k \in \mathbb{Z}$ are possible. In this embodiment, if the Nyquist-type rate condition:

$$\max_k T_k < \frac{\pi}{\Omega} \text{ where } T_k = t_{k+1} - t_k \quad (3)$$

is satisfied, the bandlimited input signal $u = u(t)$, $t \in \mathbb{R}$, can be recovered as:

$$u(t) = \sum_{l \in \mathbb{Z}} c_l g(t - s_l) \quad (4)$$

where $$s_l = (t_l + t_{l+1})/2 \text{ and } g(t) = \frac{\sin(\Omega t)}{\pi t}$$

is the impulse response of an ideal lowpass filter (LPF) with cutoff frequency $\Omega$. The set of coefficients $c_l$, $l \in \mathbb{Z}$ satisfy the system of linear equations:

$$\sum_{l \in \mathbb{Z}} \underbrace{c_l}_{[c]_l} \underbrace{\int_{t_k}^{t_{k+1}} g(s - s_l)ds}_{[G]_{kl}} = \underbrace{q_k}_{[q]_k} \quad (5)$$

for all $k \in \mathbb{Z}$. The matrix G and vectors q and c verify the linear equation $Gc = q$.

One method of signal recovery, as disclosed herein, uses an overlapping sequence of finite-dimensional coverings of the infinite-dimensional system. The method can be (i) insensitive with respect to the TEM parameters, (ii) highly efficient and stable and, (iii) implemented in real-time. The method is based on the observation that the recovery of time encoded signals given a finite number of observations has the property that the quality of signal recovery is very high in a reduced signal range. Generally, according to the disclosed subject matter, a local representation of the time-encoded signal can be obtained using a Vandermonde formulation of the recovery algorithm. Once the signal values are obtained from a finite number of possibly overlapping observations, the reduced-range segments can be stitched together. The signal obtained by segment stitching can be finally filtered for improved performance in recovery.

In one embodiment, finite-dimensional recovery algorithms can recover a signal by considering a set of trigger values $[t_i, t_{i+N}]$, $i \in \mathbb{Z}$, of the real line $\mathbb{R}$, where N is an arbitrary positive integer. Using finite windows of time triggers to solve for an infinite set of time triggers, we can solve for $u(t)$ over a restricted range, or where $t \in [t_{i+m}, t_{i+N-M}]$, for given integers i, $N > 1$, and $0 < M < N/2$.

In this embodiment $u(t)$ on $[t_i, t_{i+N}]$ can be approximated by the periodic bandlimited signal:

$$u_i(t) = \sum_{n=0}^{N} j\left(\Omega - n\frac{2\Omega}{N}\right) d_{i,n} e^{j(-\Omega + n\frac{2\Omega}{N})t} \quad (6)$$

where $d_{i,n}$ is a set of coefficients whose values are to be determined. The bandwidth of the period of $u_i(t)$ are $\Omega$ and $2N\pi/\Omega$ (for $N \geq 1$), respectively. Moreover, the coefficients $[d_i]_n = d_{i,n}$, satisfy the matrix equation $$V_i d_i = D_i P q_i \quad (7)$$

for all $i \in \mathbb{Z}$, where $[V_i]_{nm} = e^{jm2\Omega t_{i+n}/N}$ is a Vandermonde matrix, $D_i = \text{diag}(e^{j\Omega t_{i+n}})$ is a diagonal matrix, P is an upper triangular matrix with values $[P]_{nm} = 1$ and $[P]_{nm} = 0$ for $n < m+1$ and $n \geq m+1$, respectively and $[q_i]_n = q_i + n$, for all n, m=0, ..., N.

The Vandermonde system $V_i d_i = D_i P q_i$ can be solved for $d_i$ by the Björk-Pereyra algorithm: Let $z_n^m = e^{jm2\Omega t_{i+n}/N}$ where n, m=0,1, ..., N, and $b = D_i P q_i$. The system of N+1 linear equations can be solved as follows:

for n=0, ..., N-2 do:
    for m=N, ..., n+1 do:

$$b_m = (b_m - b_{m-1})/(z_m - z_{m-n-1})$$

for n=N-2, ..., 0 do:
    for m=n, ..., N-2 do:

$$b_m = b_m - b_{m+1} z_n \quad (8)$$

Following the recursion in Equation 8, $d_i = b$.

In one embodiment, both sides of Equation 7 can be multiplied by $V_i^H$, where the superscript $^H$ stands for conjugate-transposition, transforming Equation 7 into the normal equation:

$$V_i d_i = D_i P q_i \quad (9).$$

Since $V_i^H V_i$ is a Toeplitz matrix with elements $\Sigma_{l=0}^N e^{(m-n)2\Omega t_{i+l}/N}$, Equation 9 is essentially equivalent to the Toeplitz formulation disclosed in A. A. Lazar, E. K. Simonyi, and L. T. Tóth, "Fast Recovery Algorithms of Time Encoded Bandlimited Signals," *Proceeding of the International Conference on Acoustics, Speech and Signal Processing* (ICASSP'05), Philadelphia, Pa., Mar. 19-23, 2005, Vol. 4, pp. 237-240, 2005, which is incorporated by reference. Equation 9 can offer a significant benefit in terms of computational complexity for larger linear systems, when the matrix-vector multiplications in the recursive solution can be sped up by using the FFT algorithm on an augmented circular system.

In some embodiments, the oscillator can be described by a periodic orbit in the phase space. In such embodiments, the TEM with multiplicative coupling and feedback can be described by the ASDM shown in FIG. 4, where the integrator's 401 time constant $\kappa$ and the Schmitt-trigger's 402 height b and width $\delta$ are the circuit parameters. Since $\delta_{k+1} - \delta_k = 2\kappa\delta$ holds:

$$q_k = \int_{t_k}^{t_{k+1}} u(s)ds = (-1)^k (2\kappa\delta - bT_k). \quad (10)$$

Additionally, the bounds for $T_k$ give:

$$\frac{2\kappa\delta}{b+c} \le T_k \le \frac{2\kappa\delta}{b-c} \text{ and } r = \frac{2\kappa\delta}{b-c} \cdot \frac{\Omega}{\pi} < 1. \quad (11)$$

Further, as $$q_{k+1} + q_k = \int_{t_k}^{t_{k+2}} u(s)ds = (-1)^k b(T_{K+1} - T_K) \quad (12)$$

for all $k \in \mathbb{Z}$, the TEM parameter values of $\kappa$ and $\delta$ need not be known. A TDM or recovery algorithm based on this equation of $q_{k+1}+q_k$ can be called "parameter-insensitive" because it does not rely on the TEM parameter values of $\kappa$ and $\delta$. The Vandermonde system of Equation 7 can be reduced to an underdetermined linear system, whose minimum-least-square and minimum-norm solution is given by:

$$d_i = b\left(x_i - \frac{1}{\alpha_i} y_i y_i^H x_i\right) \quad (13)$$

where $\alpha_i = y_i^H y_i$ and $x_i$ and $y_i$ denote the solutions of the Vandermonde systems $V_i x_i = D_i$ $(P - ab^H)r_i$ and $V_i y_i = D_i a_i$ respectively, where $[r_i]_n = (-1)^{i+n+1} T_{i+n}$ does not depend on $\kappa\delta$, $a^H = [\ldots, 0, 1, 0, 1]$, and $b^H = [0, \ldots, 0, 0, 1]$.

Figure 6:
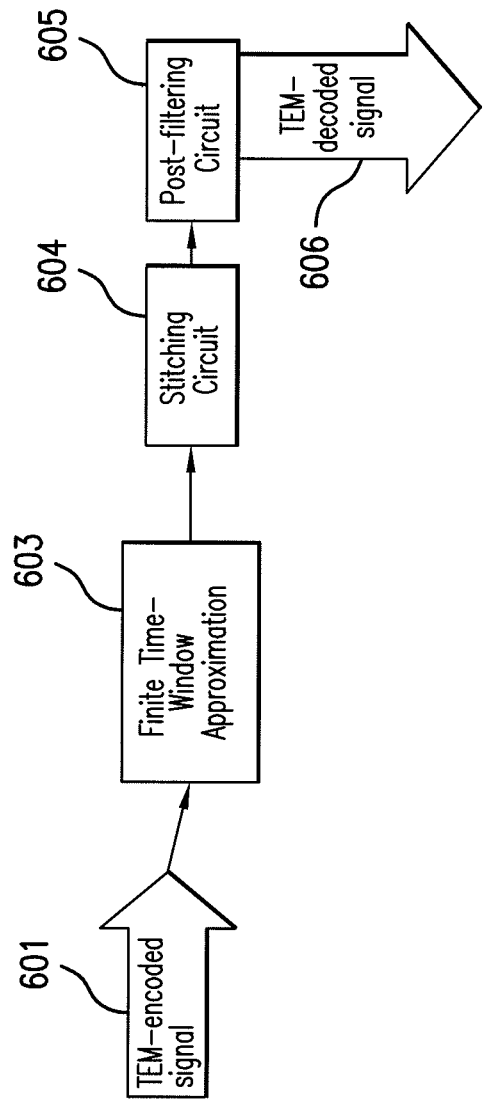
FIG. 6 is a diagram of decoding a TEM-encoded signal in accordance with some embodiments of the disclosed subject matter.

In one embodiment, because approximations can be achieved within finite time intervals, as described above, reconstruction of the overall input signal $u(t)$ on the real line can be carried out by (i) carrying out approximations in different intervals, (ii) cutting out the accurate parts by appropriate windows with finite support in the time domain and forming a partition of unity, (iii) summing up the windowed approximations, and (iv) carrying out post-processing. As depicted in FIG. 6, a TEM-encoded signal 601 can be approximated over a finite time-window 603. The approximated signal over a finite time-window can then be fed to a stitching circuit 604 to be stitched together with preceding or subsequent finite time-window approximations. Finally, the output of the stitching circuit 604 can be fed to a post-filtering circuit 605, before the decoded signal 606 is produced.

Splitting the encoded signal into windows can be achieved by many different methods. For example, the Wavelet theory can be used to define windows. In one embodiment, variable windows, determined by trigger times, can be used. In this embodiment, the windows can overlap over a certain number of trigger times. The number of trigger times that overlap in adjacent windows will be subsequently denoted by K. Using the notation $J=N-2M-K$, $\tau_n = t_{nJ+M}$, $\sigma_n = t_{nJ+M+K}$ the windows can be defined as:

$$\omega_n(t) = \begin{cases} 0 & \text{if } t \notin (\tau_n, \sigma_{n+1}], \\ \theta_n(t) & \text{if } t \in (\tau_n, \sigma_n], \\ 1 & \text{if } t \in (\sigma_n, \tau_{n+1}], \\ 1 - \theta_{n+1}(t) & \text{if } t \in (\tau_{n+1}, \sigma_{n+1}] \end{cases} \quad (14)$$

where the $\theta_n(t)$'s are appropriately chosen functions.

In some embodiments, an appropriate function for $\theta_n(t)$ can be:

$$\theta_n(t) = \sin^2\left(\frac{\pi}{2} \cdot \frac{t - \tau_n}{\sigma_n - \tau_n}\right). \quad (15)$$

Figure 5:
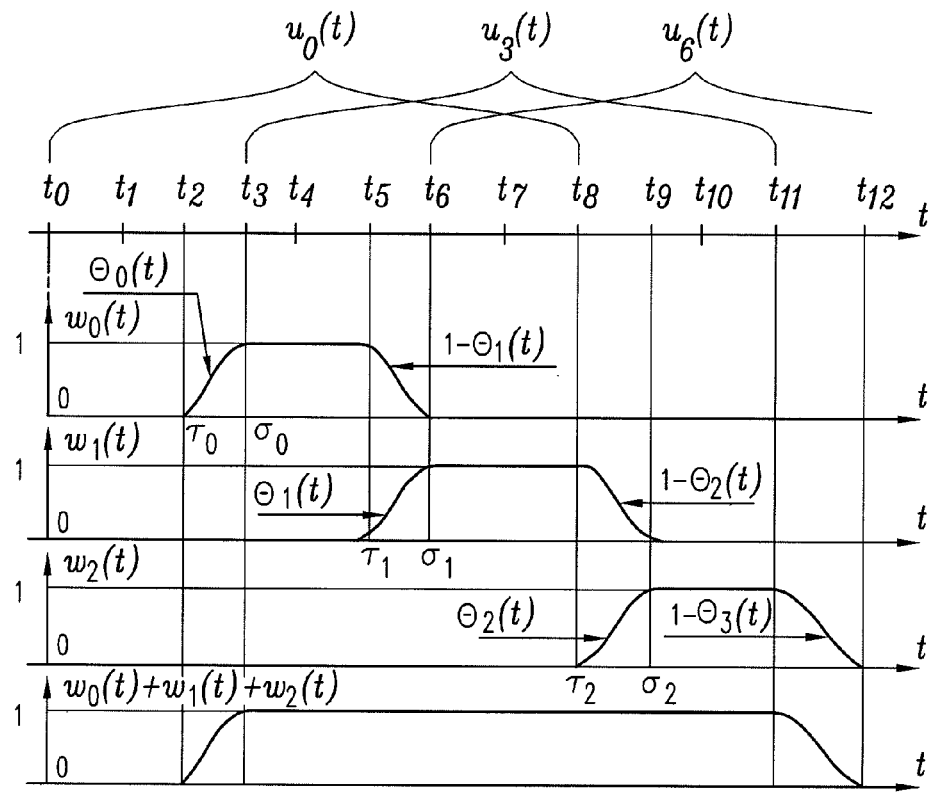
FIG. 5 depicts a set of windows in accordance with some embodiments of the disclosed subject matter.

FIG. 5 depicts windows wherein $t_o=0$, $N=8$, $M=2$, and $K=1$. Stitching the finite dimensional coverings together can yield a natural approximation of the bandlimited signal:

$$u = u(t), t \in \mathbb{R}, \text{ with } \hat{u}(t) = \sum_{n \in \mathbb{Z}} \omega_n(t) u_{nJ}(t). \quad (16)$$

In some embodiments, samples of the reconstructed signal $\hat{u}(t)$, taken uniformly with appropriate sampling period S, can be calculated. In this way the reconstructed signal can be processed by standard digital algorithms. In some embodiments, because the bandwidth of $u_{nJ}(t)$ is $\Omega$, the bandwidth of the product $u_{nJ}(t)\omega_n(t)$ in Equation 16, and thus that of $\hat{u}(t)$, is $\Omega + \nu$. Therefore, in those embodiments, for $$S \le \frac{\pi}{\Omega + \nu},$$

aliasing can be reduced or avoided.

In some embodiments, the reconstructed signal in discrete-time can be given by $\hat{u}(kS) * h[k]$, where the $h[k]$ is the impulse response of a discrete-time LPF with (digital) cutoff frequency $\pi/(1+\nu/\Omega)$ and * denotes the convolution. Because the reconstruction error spreads over the range $\epsilon\omega(-\Omega-\nu, \Omega+\nu)$, lowpass filtering can further improve the overall accuracy. Additionally, the Nyquist rate of the samples can be recovered via decimating the filtered reconstructed samples. In other embodiments, depending on the application, approximating the original samples $u(kS)$ can yield better results than approximating the filtered samples $u(kS)*h[k]$.

In some embodiments, increasing N can improve the accuracy of reconstruction as well as broaden $\omega_n(t)$ in the time domain, and hence decrease $\nu$. However, increasing N can also increase the condition number of the Vandermonde systems. In some embodiments, by appropriately choosing the parameter K and $\theta(t)$ in Equation 14, $\nu$ can be decreased for fixed N and M. For example, a frequency localization for $W_n(\omega)$ can be achieved by using $$\theta_n(t) = \sin^2\left(\frac{\pi}{2} \cdot \frac{t - \tau_n}{\sigma_n - \tau_n}\right),$$

while both $\omega_n$ and its derivative are continuous.

In some embodiments, post-filtering can be employed by accounting for the error, $e[k]=u(kS)-\hat{u}(kS)$, where $$e^{ap}[k] = \sum_{-\infty}^{\infty} \omega_n(kS) e_n^{ap}(kS)$$

and S represents the sampling rate. Where filtering with $h[k]$ impulse response, the error $\tilde{e}[k]=e[k]*h[k]$.

In one embodiment, since the $t_k$'s form a strictly increasing sequence of k, a practical reconstruction algorithm cannot use these values because of potential overflow. However, the $T_k$'s are bounded by $\pi/\Omega$, as seen in Equation 3, and as such a reconstruction algorithm that only uses $T_k$'s can be beneficial.

In this embodiment, the samples of the windows employed can be generated without using large sampling times. Because $\omega_n(t)=0$ for $t \le \tau_n$, where $\tau_n$ is monotonically increasing with n, as seen in Equation 14, the first sample occurs at $\lceil \tau_n/S \rceil$, where $\lceil\ \rceil$ is the ceiling operation. For a window shifted towards the origin as $\omega_n(t+l_n S)$, for an appropriate positive integer $l_n$, $\omega_n(t+l_n S)=0$ for $t+l_n S \le \tau_n$, i.e., for $t \le \tau_n - l_n S$. The first sample of the shifted window occurs at $\lceil (\tau_n - l_n S)/S \rceil$ and $\omega_n(\lceil \tau_n/S \rceil) = \omega_n(\lceil \tau_n - l_n S)/S \rceil)$. As a result, window samples can be generated by using a bounded set of independent variables after shifting the window close to the origin by appropriate integer multiples of the (given) sampling period.

As for the matrix parameters in the finite-dimensional coverings, no problems arise with the $r_i$'s. The $D_i$'s and the $V_i$'s are determined, on the other hand, by the trigger times through $e^{-j\Omega t_{i+n}}$ and $e^{jm2\Omega t_{i+n}/N}$, respectively. Using the periodicity of the complex exponentials, $e^{-j\Omega t_{i+n}} = e^{-j\Omega t_{i+n} + M_{i,n}2\pi}$ and $e^{jm2\Omega t_{i+n}/N} = e^{jm2\Omega t_{i+n}/N - K_{i,m,n}2\pi}$, where $M_{i,n}$ and $K_{i,m,n}$ are arbitrary integers. Choosing $M_{i,n}$ and $K_{i,m,n}$ appropriately, the exponentials can be generated by a bounded set of quantities.

In some embodiments, TEMs and TDMs can be used in Human Area Networking (HAN). Human Area Networks use the human body to transmit data between devices. These signals can be between data collection devices and sensors, such as pacemakers, glucose monitors, pulseoximeters, electrocardiography (ECG) machines, and electroencephalography (EEG) machines, or between consumer electronics, such as cellphones or music players.

One important aspect to HAN design and implementation is energy efficiency. This is especially true in certain biomedical or health-monitoring applications such as pacemakers, glucose monitors, pulseoximetry, electrocardiography (ECG), and electroencephalography (EEG). In contrast, for some applications, the requirements for accuracy and speed (bandwidth) are rather modest. For example, 8-bit accuracy and 100-500 Hz bandwidth is typical in ECG and EEG systems, as described by E, V. Aksenov, Yu. M. Ljashenko, A. V. Plotnikov, D. A. Prilutskiy, S. V. Selishchev, E. V. Vetvetskiy, "Biomedical data acquisition systems based on sigma-delta analogue-to-digital converters" in *Proc. IEEE EMBS 23rd Annual International Conference*, October 2001, vol. 4, pp, 3336-3337, which is incorporated by reference. In these examples, the energy consumption of the body-mounted sensors can be a critical factor. In some embodiments, the body-mounted sensors connect to a data-collector. The data collector can be any device capable of storing and/or relaying data or electronic signals such as a radio device, mobile telephone, personal digital assistant (PDA), or enhanced wristwatch. For simplicity sake, when referring to a PDA in the remainder of this disclosure, any data collector can be used. In some embodiments, more power can be assigned to the data collector, placed close to or on the human body. Further, in some embodiments, the sensor signals can be evaluated at a remote site (center) where practically unlimited power can be assumed.

The technological evolution of low-power integrated circuits (ICs), and wireless communication allows the production of low-cost, miniature, lightweight, intelligent physiological sensors. These units enable the deployment of sensor networks for health monitoring often referred to as human, personal or body area networks. In these solutions analog-to-digital (A/D) conversion and wireless digital transmission is carried out by the sensor nodes using radio-frequency (RF) channels via tiny antennas. Power dissipation due to both A/D conversion and digital transmission are two major limitations. In typical recent RF applications the amount of energy needed for transmitting one single bit amounts to that of executing about 1000 32-bit computations.

Figure 7:
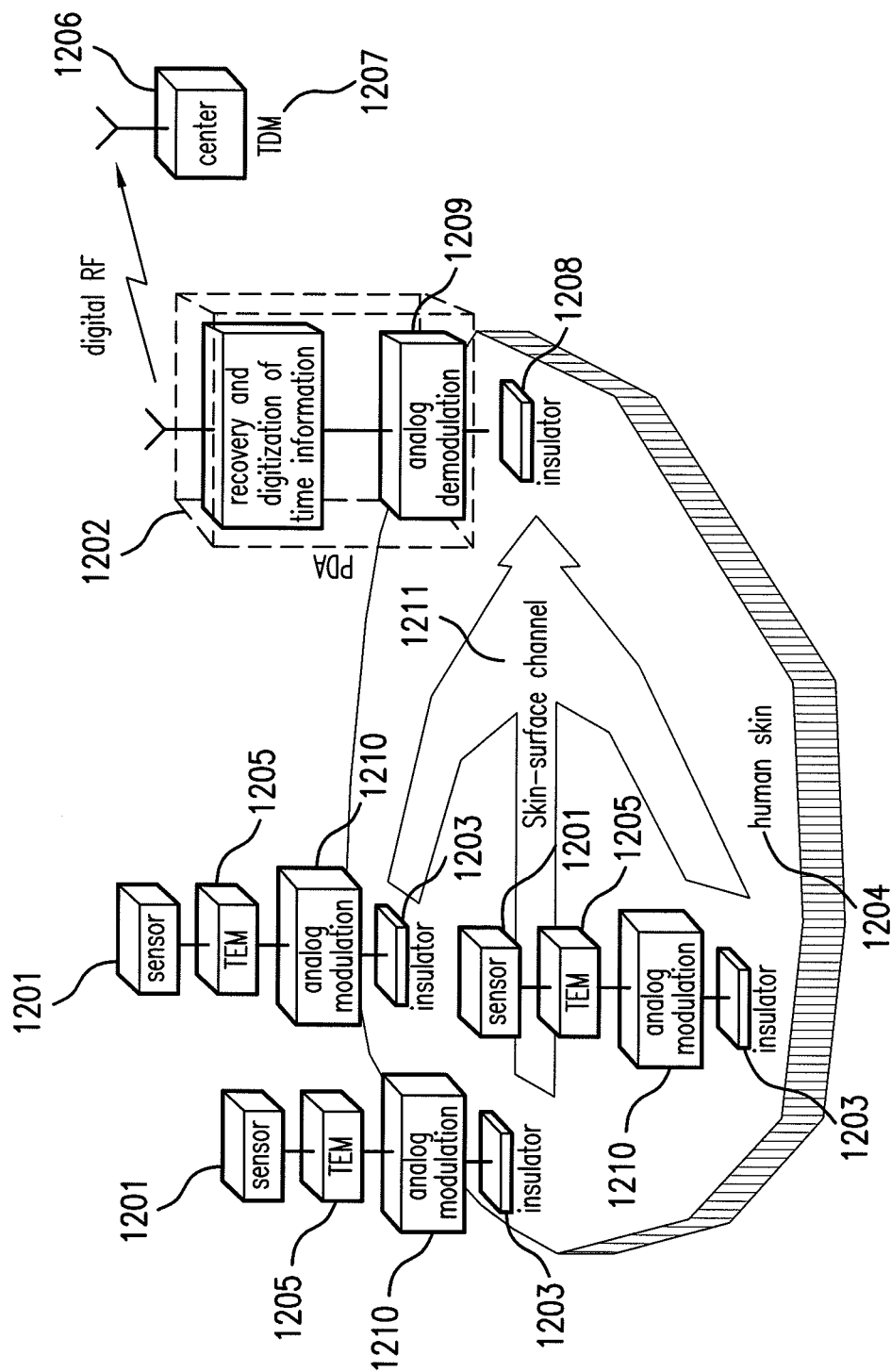
FIG. 7 depicts a Human Area Network in accordance with some embodiments of the disclosed subject matter.

FIG. 7 depicts an embodiment of the disclosed subject matter using an HAN for biomonitoring. As shown, several sensors 1201 and the PDA 1202 can be connected to the human body via insulators 1203. The transmit power can be reduced by using the skin surface 1204 as a short range communication channel as the skin-surface channel 1211 has been shown to have substantially less power requirements compared to RF channels. Other parts of a body can be used to transmit data such as bone or body fluids. Connections with any of these body parts can be made via a body interface mechanism such as an insulator. Briefly, since any two distinct points of the human body are interconnected via capacitive coupling, signals with high enough frequency content can travel between any two points. Whereas a radio transmitting PAN device needs to be operated at frequencies in the MHz-to-GHz range in order to efficiently transmit biomonitoring information, electrostatic coupling can reach the same efficiency by running the devices at much lower frequencies (0.1 to 1 MHz). Given that the energy consumption of electronic devices increases with frequency, substantial amount of energy can be saved. Further, data transmitted through the human body can eventually escape through the feet into the ground, thereby minimizing the chance of intercept and, thus, providing secure communications.

As further depicted in FIG. 7, the collected biomonitoring information can be represented in the time domain with Time Encoding Machines (TEMs) 1205. The output of the TEMs can undergo analog modulation 1210 for increased frequency content. The TEM-encoded data can then be transmitted through the insulator 1203 into the skin 1204. After strong attenuation and often corruption by noise and/or low-frequency interference, the aggregate of the modulated signals can be recovered at another location of the human body via another insulator 1208. The received signal can be first demodulated 1209 after the appropriate sensor is selected. Based on the demodulator output, the PDA 1202 can either decode the data using a TDM, or determine the time information contained in the demodulated (selected) signal and forward it in digital form to the remote center 1206 for reconstruction via a TDM 1207.

Figure 8:
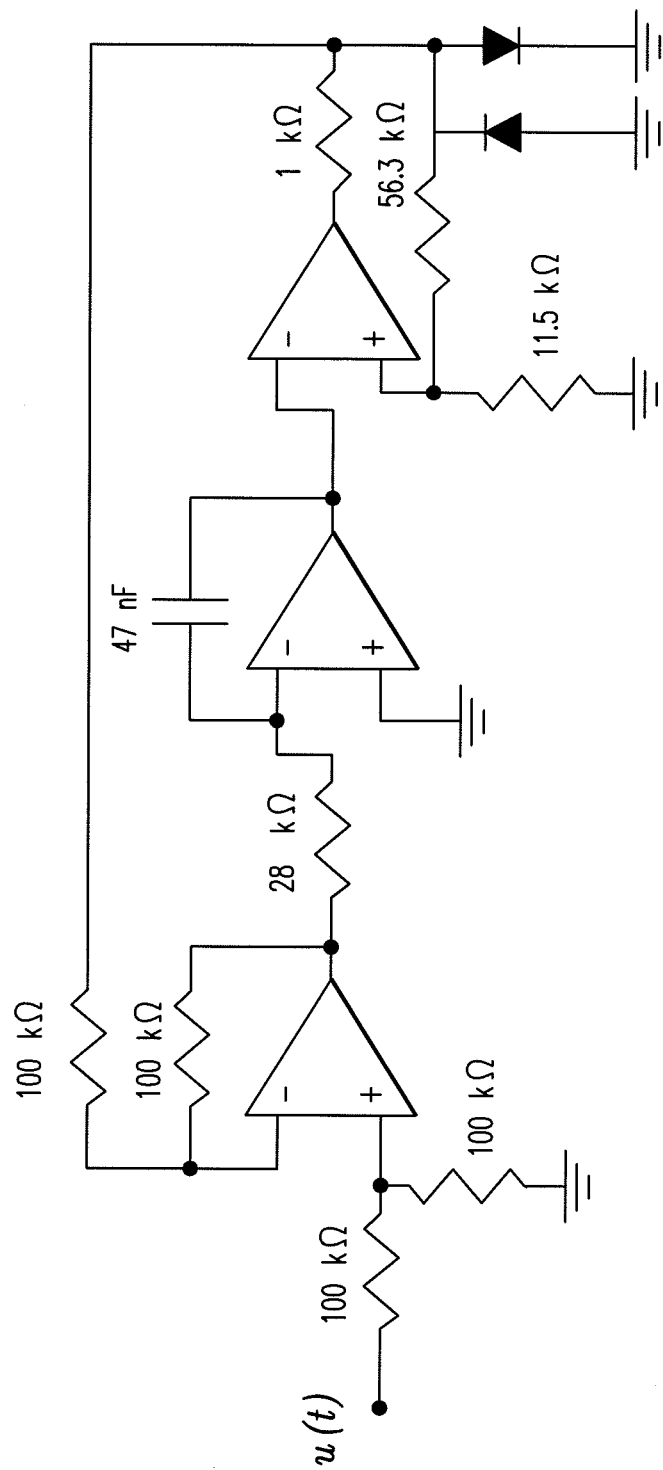
FIG. 8 depicts a sample Time Encoding Machine in accordance with some embodiments of the disclosed subject matter.

The TEM 1205, modulator 1210, and demodulator 1209 can be implemented using standard discrete-component circuit elements and commercially available ICs. FIG. 8 depicts an example embodiment of a TEM 1205 using resistors and capacitors with 2% tolerance, LF256 opamps, and diodes. The middle opamp with the 47 nF capacitor and 28 k resistor implements the integrator. The rightmost opamp with resistors 1 kΩ, 56.3 kΩ, 11.5 kΩ, and the diodes can realize the Schmitt trigger. The diodes can force the Schmitt-trigger output to take voltages around ±0.6 V independent of the ±9 V power supply voltages of the opamps. The adder implemented by the leftmost opamp and the 100 k resistors allow measuring the sum of u(t) and the Schmitt-trigger output for test purposes.

Figure 9:
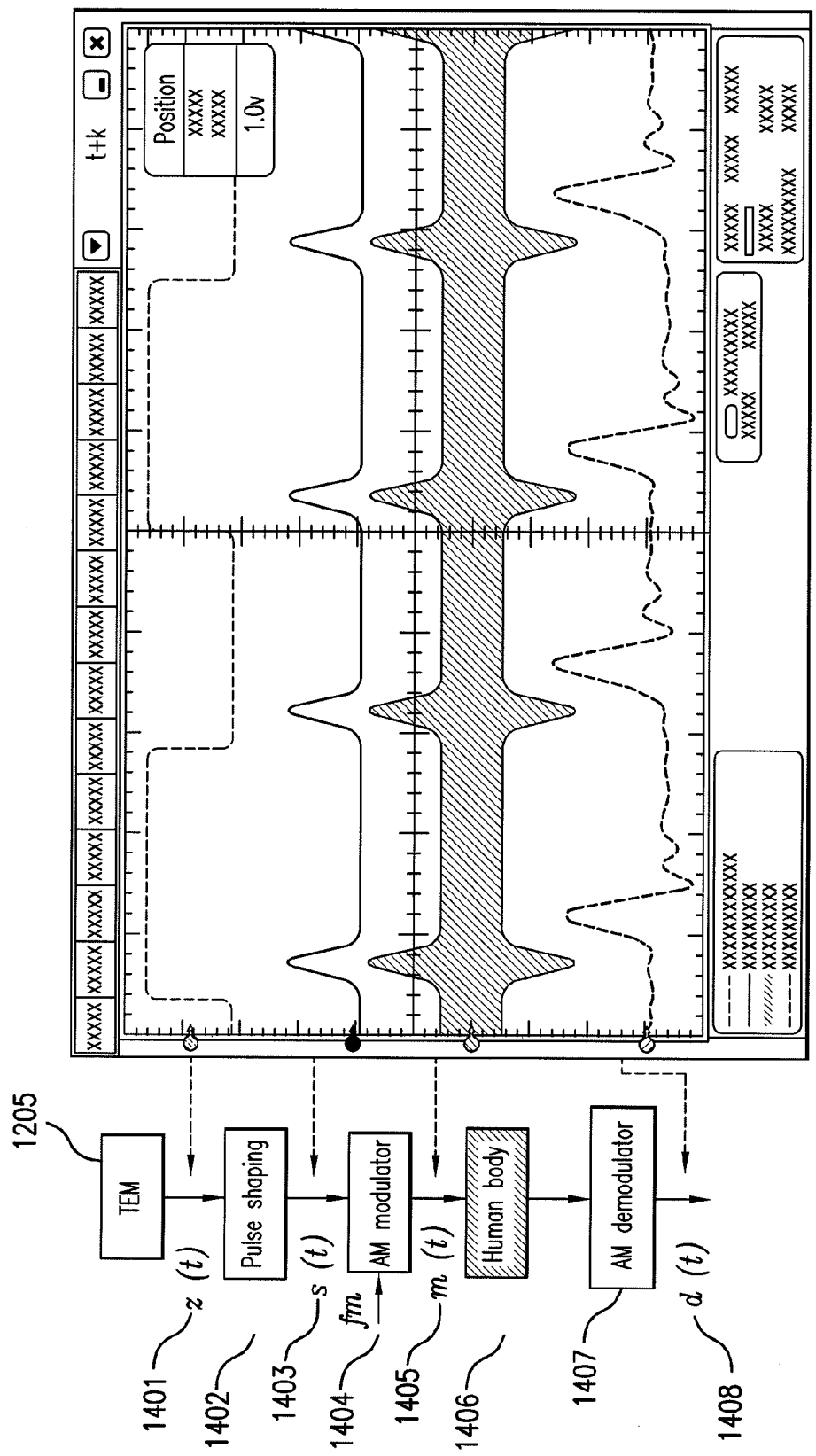
FIG. 9 depicts a schematic of modulation and demodulation for a Human Area Network implemented in accordance with some embodiments of the disclosed subject matter.

FIG. 9 depicts modulation and demodulation according to the disclosed subject matter. First, s(t) 1403 can be created by pulse shaping 1402 z(t) 1401. The value of m(t) 1405 can be obtained by AM-modulating 1404 s(t) 1403 with a rectangular carrier. The value of d(t) 1408 is the AM demodulator 1407 output of a sensitive receiver. In one embodiment, the receiver can be built with a CSF455 type ceramic filter and the TDA 1046 chip. In some embodiments, the receiver can be highly sensitive to counteract the strong and unpredictable attenuation of a skin-surface channel 1211.

Figure 10:
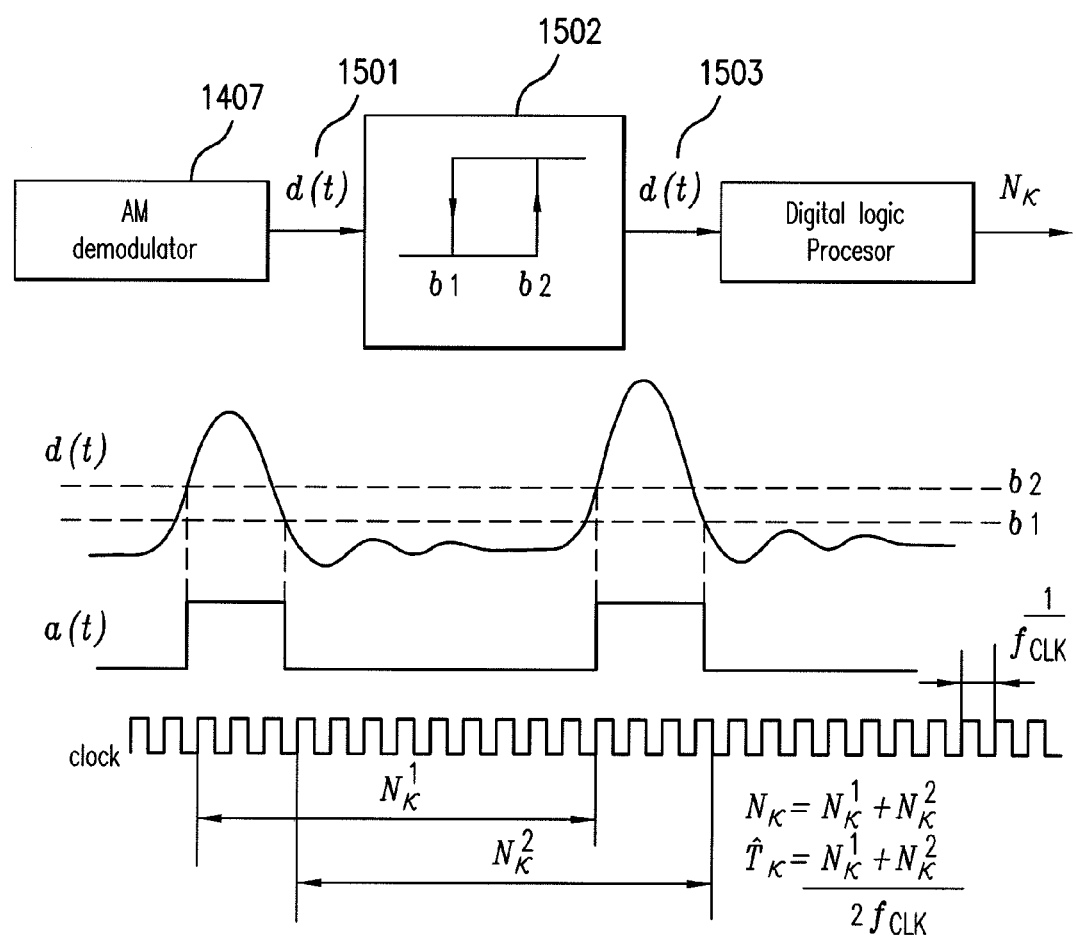
FIG. 10 depicts the results of an AM-demodulator in accordance with some embodiments of the disclosed subject matter.

In one embodiment of a HAN, the PDA can recover the $T_k$'s from the demodulator output d(t), digitize them, and forward the digitized $T_k$'s for signal reconstruction at the remote site. In some embodiments, an approximation of the $T_k$'s using a simple level-crossing scheme, as shown in FIG. 10, can be implemented. From the output 1503 of a comparator with hysteresis (Schmitt trigger) 1502 fed by d(t) 1501 and a time-measuring clock, the digitized $T_k$'s can be obtained by counting clock cycles and applying the formula, $$\hat{T}_k = \frac{N_k^1 + N_k^2}{2 f_{CLK}}.$$

The clock frequency $f_{CLK}$ can be known at the center (remote site). A software module can carry out this algorithm using the samples of the demodulator output delivered by the digital oscilloscope.

The disclosed subject matter and methods can be implemented in software stored on computer readable storage media, such as a hard disk, flash disk, magnetic tape, optical disk, network drive, or other computer readable medium. The software can be performed by a processor capable of reading the stored software and carrying out the instructions therein.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within the spirit and scope of the disclosed subject matter.

The invention claimed is:

1. A circuit for decoding a signal encoded by a Time Encoding Machine (TEM) comprising:
   a Time Decoding Machine (TDM) for decoding a portion of a TEM-encoded signal, the TEM-encoded signal comprising a plurality of action potentials encoded in a time sequence, said TDM comprising a TDM-input and a TDM-output, said TDM-input for receiving the portion of the TEM-encoded signal over a first time-window, said TDM-output for transmitting a decoded approximated signal over said first time-window; and
   a stitching circuit, having a stitching-input connected to said TDM-output, said stitching circuit combining said decoded approximated signal over said first time-window with at least one other decoded approximated signal over a second time-window, wherein said first time-window and said second time-window overlap.

2. The circuit of claim 1 wherein said TDM calculates a value of said TEM-encoded signal, u, over said first time-window, $[t_i, t_{i+N}]$, wherein the value of u at a given time, t, is approximated by solving for periodic bandlimited signal $$u_i(t) = \sum_{n=0}^{N} j\left(\Omega - n\frac{2\Omega}{N}\right) d_{i,n} e^{j\left(-\Omega + n\frac{2\Omega}{N}\right)t};$$

where bandwidths of each period of $u_i(t)$ are $\Omega$ and $2N\pi/\Omega$ (for $N \geq 1$), respectively;
coefficients $[d_i]_n = d_{i,n}$, and $d_i$ is solved by letting $z_n^m = e^{j m 2\Omega t_{i+n}/N}$ where n, m=0,1, ..., N, and solving for a vector b such that
   for n=0, ..., N−2 do:
      for m=N, ..., n+1 do:

$b_m = (b_m - b_{m-1})/(z_m - z_{-m-1})$ for n=N−2, ..., 0 do:
      for m=n, ..., N−2 do:

$b_m = n_m - b_{m+1} z_n$ and $d_i = b$.

3. The circuit of claim 2 wherein $$d_i = b\left(x_i - \frac{1}{\alpha_i} y_i y_i^H x_i\right),$$

for $\alpha_i = y_i^H y_i$ and $x_i$ and $y_i$ denote solutions of Vandermonde systems $V_i x_i = D_i (P - ab^H) r_i$ and $V_i y_i = D_i a_i$ respectively;
   where $[V_i]_{nm} = e^{j m 2\Omega_i/N}$ is a Vandermonde matrix,
   $D_i = \text{diag}(e^{j\Omega t_{i+n}})$ is a diagonal matrix,
   P is an upper triangular matrix with values $[P]_{nm}=1$ and $[P]_{nm}=0$ for n<m+1 and n≥m+1,
   $[r_i]_n = (-1)^{i+n+1} T_{i+n}$
   $a^H = [\ldots, 0, 1, 0, 1]$, and
   $b^H = [0, \ldots, 0, 0, 1]$.

4. The circuit of claim 2 wherein said coefficients $[d_i]_n = d_{i,n}$ are recovered by solving equation $V_i^H V_i d_i = V_i^H D_i P q_i$, where $V_i^H$ is a conjugate transposition of $V_i$,
   $[V_i]_{nm} = e^{j m 2\Omega t_{i+n}/N}$ is a Vandermonde matrix,
   $D_i = \text{diag}(e^{j\Omega t_{i+n}})$ is a diagonal matrix,
   P is an upper triangular matrix with values $[P]_{nm}=1$ and $[P]_{nm}=0$ for n<m+1 and n≥m+1, respectively and
   $[q_i]_n = q_i + n$, for all n, m=0, ..., N.

5. The circuit of claim 2, wherein said first and second time-windows, $\omega_n$, are defined by a function $$\omega_n(t) = \begin{cases} 0 & \text{if } t \notin (\tau_n, \sigma_{n+1}], \\ \theta_n(t) & \text{if } t \in (\tau_n, \sigma_n], \\ 1 & \text{if } t \in (\sigma_n, \tau_{n+1}], \\ 1 - \theta_{n+1}(t) & \text{if } t \in (\tau_{n+1}, \sigma_{n+1}], \end{cases}$$

where K represents a value of desired overlapping trigger times, J=N−2M−K, $\tau_n = t_{nJ+M}$, $\sigma_n = t_{nJ+M+K}$, N represents a number of trigger times and $$\theta_n(t) = \sin^2\left(\frac{\pi}{2} \cdot \frac{t - \tau_n}{\sigma_n - \tau_n}\right).$$

6. The circuit of claim 5, wherein said stitching circuit combines said first and second time-windows by solving equation $$\hat{u}(t) = \sum_{n \in Z} \omega_n(t) u_{nJ}(t).$$

7. The circuit of claim 1 further comprising a post-filtering circuit connected to an output of said stitching circuit for receiving a combined TEM-decoded signal, said post-filtering circuit removing an approximate error, $e[k] = u(kS) - \hat{u}(kS)$, from said combined TEM-decoded signal of said stitching circuit by solving for an equation $$e^{ap}[k] = \sum_{n \in Z} \omega_n(kS) e_{nJ}^{ap}(kS),$$

where S represents a sampling rate of said TEM-encoded signal.

8. A method for decoding a signal encoded by a Time Encoding Machine (TEM) comprising:
   defining a plurality of time-windows, each time-window corresponding to a portion of a TEM-encoded signal and comprising a plurality of trigger values, the TEM-encoded signal comprising a plurality of action potentials encoded in a time sequence, at least two of said time-windows overlapping;

decoding each of said time-windows using a Time Decoding Machine (TDM) to generate a decoded time-window; and stitching said decoded time-windows together to generate a TEM-decoded signal.

9. The method of claim 8 wherein each of said time-windows overlaps with at least one other time-window.

10. The method of claim 8 wherein said TDM calculates a value of said TEM-encoded signal, u, over one of said plurality of time-windows, $[t_i, t_{i+N}]$, where the value of u at a given time, t, is approximated by solving for periodic band-limited signal $$u_i(t) = \sum_{n=0}^{N} j\left(\Omega - n\frac{2\Omega}{N}\right) d_{i,n} e^{j\left(-\Omega + n\frac{2\Omega}{N}\right)t};$$

where bandwidths of each period of $u_i(t)$ are $\Omega$ and $2N\pi/\Omega$ (for $N \geq 1$), respectively;

coefficients $[d_i]_n$ and $d_i$ can be solved by letting $z_n^m = e^{jm2\Omega t_{i+n}/N}$ where n, m=0,1, ... N, and solving for a vector b such that for n=0, ... ,N−2 do:
    for m=N do:

$$b_m = (b_m - b_{m-1})/(z_m - z_{m-n-1})$$

for n=N−2, ... , 0 do:
    for m=n, ... , N−2 do:

$$b_m = b_m - b_{m+1} z_n$$

and $d_i = b$.

11. The method of claim 10 wherein $$d_i = b\left(x_i - \frac{1}{\alpha_i} y_i y_i^H x_i\right),$$

for $\alpha_i = y_i^H y_i$ and $x_i$ and $y_i$ denote solutions of Vandermonde systems $V_i x_i = D_i (P - ab^H) r_i$ and $V_i y_i = D_i a_i$ respectively;

where $[V_i]_{nm}$ is a Vandermonde matrix,
$D_i = \text{diag}(e^{j\Omega t_{i+n}})$ is a diagonal matrix,
P is an upper triangular matrix with values $[P]_{nm} = 1$ and $[P]_{nm} = 0$ for $n < m+1$ and $n \geq m+1$,
$[r_i]_n = (-1)^{i+n+1} T_{i+n}$,
$a^H = [\ldots, 0, 1, 0, 1]$, and
$b^H = [0, \ldots, 0, 0, 1]$.

12. The method of claim 10 wherein said coefficients $[d_i]_n = d_{i,n}$ are recovered by solving equation $V_i^H V_i d_i = V_i^H D_i P q_i$, where $V_i^H$ is a conjugate transposition of $V_i$,
$[V_i]_{nm} = e^{jm,2\Omega t_{i+n}/N}$ is a Vandermonde matrix,
$D_i = \text{diag}(e^{j\Omega t_{i+n}})$ is a diagonal matrix,
P is an upper triangular matrix with values $[P]_{nm} = 1$ and $[P]_{nm} = 0$ for $n < m+1$ and $n \geq m+1$, respectively and
$[q_i]_n = q_i + n$, for all n, m=0, N.

13. The method of claim 10, wherein said time-windows, $\omega_n$, are defined by a function $$\omega_n(t) = \begin{cases} 0 \text{ if } t \notin (\tau_n, \sigma_{n+1}], \\ \theta_n(t) \text{ if } t \in (\tau_n, \sigma_n], \\ 1 \text{ if } t \in (\sigma_n, \tau_{n+1}], \\ 1 - \theta_{n+1}(t) \text{ if } t \in (\tau_{n+1}, \sigma_{n+1}], \end{cases}$$

where K represents a value of desired overlapping trigger times, J=N−2M−K, $\tau_n = t_{nJ+M}$, $\sigma'' = t_{nJ+m+K}$, N represents a number of trigger times and $$\theta_n(t) = \sin^2\left(\frac{\pi}{2} \cdot \frac{t - \tau_n}{\sigma_n - \tau_n}\right).$$

14. The method of claim 13, wherein said stitching comprises adding said time-windows by solving equation $$\hat{u}(t) = \sum_{n \in Z} \omega_n(t) u_{nJ}(t).$$

15. The method of claim 8 further comprising post-filtering said TEM-decoded signal by removing an approximate error, $e[k] = u(kS) - \hat{u}(kS)$, from said TEM-decoded signal by solving for an equation $$e^{ap}[k] = \sum \omega_n(kS) e_{nJ}^{ap}(kS),$$

where S represents a sampling rate of said TEM-encoded signal.

* * * * *